(12) United States Patent
Bonne

(10) Patent No.: US 7,021,821 B2
(45) Date of Patent: Apr. 4, 2006

(54) DIFFERENTIAL THERMAL SENSORS

(75) Inventor: Ulrich Bonne, Hopkins, MN (US)

(73) Assignee: Honeywell International Inc., Morristown, NJ (US)

( * ) Notice: Subject to any disclaimer, the term of this patent is extended or adjusted under 35 U.S.C. 154(b) by 48 days.

(21) Appl. No.: 10/856,364

(22) Filed: May 28, 2004

(65) Prior Publication Data

US 2005/0265422 A1 Dec. 1, 2005

(51) Int. Cl.
*G01N 25/18* (2006.01)
(52) U.S. Cl. .......................................... 374/44; 374/10
(58) Field of Classification Search ................. 374/10, 374/11, 43, 44, 45, 54, 135
See application file for complete search history.

(56) References Cited

U.S. PATENT DOCUMENTS

| | | |
|---|---|---|
| 4,683,159 A | 7/1987 | Bohrer et al. |
| 5,439,291 A * | 8/1995 | Reading ....................... 374/11 |
| 5,711,604 A * | 1/1998 | Nakamura ................... 374/44 |
| 5,952,572 A * | 9/1999 | Yamashita et al. ........ 73/504.04 |
| 6,019,505 A | 2/2000 | Bonne et al. |
| 6,168,645 B1 | 1/2001 | Succi et al. |
| 6,322,247 B1 | 11/2001 | Bonne et al. |
| 6,361,206 B1 | 3/2002 | Bonne |
| 6,370,939 B1 * | 4/2002 | Smith et al. ................... 374/43 |
| 6,393,894 B1 | 5/2002 | Bonne et al. |
| 6,527,835 B1 * | 3/2003 | Manginell et al. ........ 73/204.26 |
| 2001/0008081 A1 * | 7/2001 | Smith et al. ................... 73/579 |
| 2001/0012312 A1 * | 8/2001 | Smith ........................... 374/43 |
| 2002/0073772 A1 * | 6/2002 | Bonne et al. ............ 73/204.11 |
| 2002/0190839 A1 * | 12/2002 | Padmanabhan et al. ....... 338/13 |
| 2003/0214057 A1 * | 11/2003 | Huang ......................... 264/1.1 |
| 2004/0250601 A1 * | 12/2004 | Lin ............................. 374/44 |

OTHER PUBLICATIONS

Panasonic—NEO-HUMICERAM High performance ceramic humidity sensor detects humidity over a wide temperature range of—20° C. to 600° C. Kitamura et al. "Humidity Sensor for Absolute Humidity Measurements and its Applications", Proceedings of the 1st Sensor Symposium, 1981, pp. 119-123.

* cited by examiner

*Primary Examiner*—G. Bradley Bennett
(74) *Attorney, Agent, or Firm*—Trevor B. Joike

(57) ABSTRACT

A sensor includes at least two microsensor chips in a housing. The chips may be arranged as (i) an absolute thermal conductivity sensor by exposing one chip to a sample fluid and the other chip to a sealed reference fluid, (ii) a differential thermal conductivity sensor by exposing the two chips to a sample fluid before and after it is modified, respectively, (iii) a one-axis rotation sensor by exposing both chips, positioned at an angle of 180° relative to one another, to a rotational flow in a toroidal chamber, (iv) a two or three axis rotation sensor by placing the two chips or three such chips on two or three orthogonal faces of a cube, (v) a one axis orientation/tilt/acceleration sensor by exposing the two chips to a fluid in a sealed toroidal chamber and by mounting the chips at an angle of substantially 90° relative to one another, (vi) a two axis orientation/tilt/acceleration sensor by placing the two chips at an angle of 90° relative to one another in a fluid filled chamber substantially without inertial flow, and (vii) a combined tilt/rotation sensor based on above (iii) by periodically adding and subtracting the signals from the two chips.

17 Claims, 3 Drawing Sheets

DIFFERENTIAL THERMAL SENSORS

TECHNICAL FIELD OF THE INVENTION

The present invention relates to the design and use of one type of thermal sensor building block for the creation of environmentally compensated sensor system embodiments of absolute and relative thermal conductivity, rotation and 1-to-3-axis tilt or acceleration.

BACKGROUND OF THE INVENTION

Thermal sensors that sense the thermal conductivity of a material such as a fluid have been used in a variety of applications including gas chromatography.

In gas chromatography, an unknown gas sample volume is injected into a carrier gas, the unknown gas is separated by the action of a separating column, and the separated sample gas components are transported by the carrier gas to and past a sensor, such as the thermal conductivity sensor, that senses changes in thermal conductivity inherent in the various components of the unknown gas. The thermal conductivity sensor responds to any component of the unknown gas whose thermal conductivity is different than that of the carrier gas. Helium is frequently used as the carrier gas because of its exceptionally high thermal conductivity.

The output of the thermal conductivity sensor peaks as each gas component passes by the thermal conductivity sensor and these peaks serve to identify each of the components of the gas by their elution timing and their concentration by their areas under the corresponding peaks. Thermal conductivity sensors available today for performing the above functions are bulky and expensive.

Present absolute thermal conductivity sensors that sense the thermal conductivity of fluids, such as gases, respond to changes in the chemical compositions of the fluids, which is generally the sensing objective. However, these present absolute thermal conductivity sensors also respond to changes in temperature, pressure, orientation, acceleration, vibration, rotation, and flow, which is generally an undesirable response of these absolute thermal conductivity sensors.

Flow disturbances, which result in an erroneously larger thermal conductivity being sensed, can be minimized by judicious sizing of the sensor housing in exchange for some loss in the speed of response. However reducing the undesirable influence of temperature, pressure, humidity, orientation, or rotation typically requires the use of additional temperature, pressure, and/or orientation sensors.

Moreover, differential thermal conductivity sensor assemblies have been used in Gas Chromatography systems where one thermal conductivity sensor is in contact with the outlet carrier gas stream carrying the separated components of an injected sample and the other thermal conductivity sensor is in contact with the inlet pure carrier gas stream. It is thought that, by placing the two thermal conductivity sensors in close proximity to one another, temperature differences experienced by the sensors are minimized and the sensors are exposed to the same flow rate. The sensors are typically oriented in the same direction.

However, the two thermal conductivity sensors in this system may be exposed to different, but steady pressures due to the pressure drop through the separation column of the gas chromatography system. Thus, such gas chromatography systems produce outputs that contain an undesired error component due to this pressure drop. Moreover, available differential thermal conductivity sensors used in these systems are typically manufactured in low volumes, with specially designed hot wire anemometers which result in the systems being very costly.

The present invention solves one or more of these or other problems.

SUMMARY OF THE INVENTION

According to one aspect of the present invention, an absolute thermal conductivity sensor comprises a housing and first and second microstructures. The housing has a channel exposed to a sample fluid whose absolute thermal conductivity is to be determined. The first microstructure sensor has a microheater and at least one temperature responsive microsensor, the first microstructure sensor is mounted to the housing so as to be exposed to the sample fluid in the channel. The second microstructure sensor has a microheater and at least one temperature responsive microsensor, the second microstructure sensor is mounted to the housing so as to be in contract only with a reference fluid and isolated from changes in composition of the sample fluid in the channel but not from common changes in temperature, pressure, orientation, and acceleration.

According to another aspect of the present invention, a rotation sensor comprises a housing and first and second microstructures. The housing has a a sealed axi-symmetric chamber containing a fluid and a rotation axis. The first microstructure sensor is mounted to the housing so as to be exposed to the fluid in the sealed chamber, and the first microstructure sensor includes a microheater and at least one temperature responsive microsensor. The second microstructure sensor is mounted to the housing so as to be exposed to the fluid in the sealed chamber, the second microstructure sensor includes a microheater and at least one temperature responsive microsensor, and the first and second microstructure sensors are mounted with respect to the axis so as sense a rotation of the housing about the axis, based on the sensors' high sensitivity to flow of the fluid relative to the housing.

According to still another aspect of the present invention, a differential thermal conductivity sensor comprises a housing and first and second microstructures. The housing has a channel exposed to a fluid whose thermal conductivity is to be determined. The first microstructure sensor is mounted to the housing so as to be exposed to the fluid in the channel, and the first microstructure sensor includes a microheater and at least one temperature responsive microsensor. The second microstructure sensor is mounted to the housing so as to be exposed to the fluid in the channel, the second microstructure sensor includes a microheater and at least one temperature responsive microsensor, the two channels are precisely of the same shape, and the first and second microstructure sensors are mounted to the housing so that there is a minimum distance between the first and second microstructure sensors and the channel as well as a minimum dead volume around each individual sensor so as to maximize differential fluid property measurement sensitivity and time resolution, with least interference by uncontrolled differences in temperature, pressure, fluid velocity, orientation and acceleration.

Accordingly to a further aspect of the present invention, a differential thermal conductivity sensor comprises a housing and first and second sensors. The housing has a channel exposed to a unprocessed fluid whose thermal conductivity is to be determined before processing the fluid. The first sensor is mounted in a first housing so as to be exposed to the unprocessed fluid in a first part of a channel. The second sensor is mounted in a second, closely co-located housing so as to be exposed to the processed fluid in a second part of the same channel.

According to yet another aspect of the present invention, an orientation sensor comprises a housing and first and second microstructure sensors. The housing has a sealed chamber containing a fluid and a rotation axis. The first microstructure sensor is mounted to the housing so as to be exposed to the fluid in the sealed chamber, and the first microstructure sensor includes a microheater and at least one temperature responsive microsensor. The second microstructure sensor is mounted to the housing so as to be exposed to the fluid in the sealed chamber, the second microstructure sensor includes a microheater and at least one temperature responsive microsensor, and the first and second microstructure sensors are mounted at an angle of substantially 90° with respect to one another so as to sense two-axis orientation of the housing, or 180° with respect to each other so as to sense one-axis orientation of the housing.

BRIEF DESCRIPTION OF THE DRAWINGS

These and other features and advantages will become more apparent from a detailed consideration of the invention when taken in conjunction with the drawings in which.

DETAILED DESCRIPTION

Figure 1:
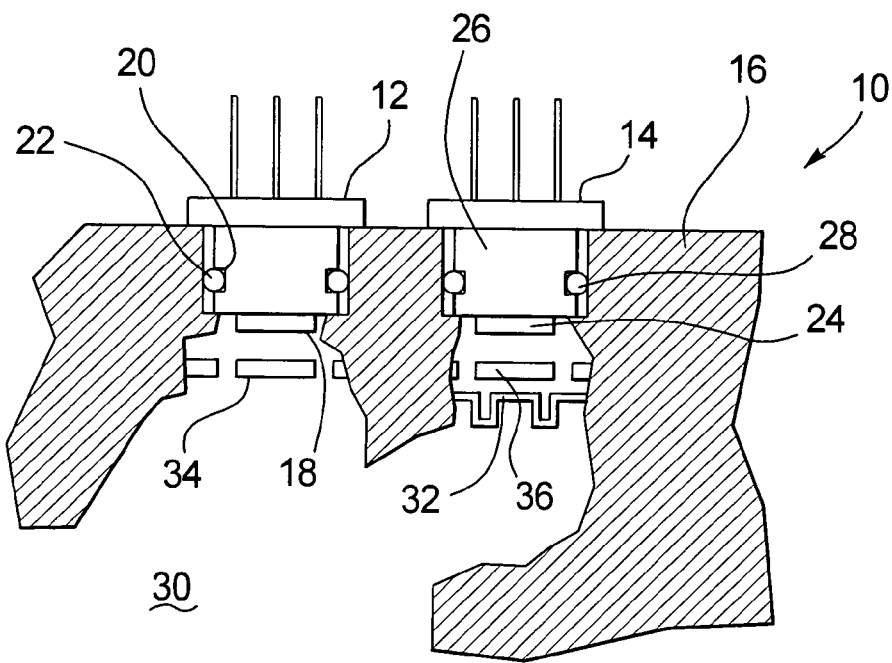
FIG. 1 illustrates an absolute thermal conductivity sensor according to a first embodiment of the present invention.

FIG. 1 shows an absolute thermal conductivity sensor 10 according to a first embodiment of the present invention. As shown in FIG. 1, the absolute thermal conductivity sensor 10 includes a first microstructure sensor 12 and a second microstructure sensor 14 mounted to a housing 16.

The first microstructure sensor 12, for example, may comprise a first microstructure 18 supported by a first mounting block 20 secured to the housing 16. A first O-ring seal 22 fitted in a recess of the first mounting block 20 seals against leakage between the housing 16 and the first mounting block 20.

The second microstructure sensor 14, for example, may comprise a second microstructure 24 supported by a second mounting block 26 secured to the housing 16. A second O-ring seal 28 fitted in a recess of the second mounting block 26 seals against leakage between the housing 16 and the second mounting block 26.

Each of the first and second microstructures 18 and 24, for example, may be constructed in accordance with the microbridge disclosed in U.S. Pat. No. 4,683,159. Thus, each of the first and second microstructures 18 and 24, for example, may be constructed as one or more temperature responsive microsensors that sense heat emitted by a microheater. More specifically, each of the first and second microstructures 18 and 24 may include a microheater between a pair of temperature responsive microsensors.

The housing 16 has a channel 30 that supports a fluid whose thermal conductivity is to be sensed. The first microstructure 18 is exposed to the fluid in the channel 30. However, a diaphragm 32 seals the second microstructure 24 from the fluid in the channel 30. A fill fluid fills the chamber formed between the diaphragm 32 and the second microstructure 24. This fill fluid, for example, may be an inert gas or liquid, which ideally is close to the average composition of the fluid typically encountered as the sample fluid in contact with the first sensor.

A first shield 34 is provided to shield the first microstructure 18 from fluid convection that detrimentally affects the accuracy in sensing the thermal conductivity of the fluid in the channel 30. A second shield 36 is provided between the second microstructure 24 and the diaphragm 32. The first and second shields 34 and 36 may be similar to the shield 25 disclosed in U.S. Pat. No. 6,322,247 and may be incorporated as part of the housing 16.

The absolute thermal conductivity sensor 10 enables the sensing of small changes in the composition of the monitored fluid in the channel 30, and is useful in those cases where forced sample and/or reference streams are not available.

The second microstructure 24 is used to cancel changes in such environmental conditions as fluid pressure, temperature, acceleration, orientation, etc. from the output of the first microstructure 18. Thus, the output of the first microstructure 18 experiences minimal interference from such environmental conditions.

Figure 2:
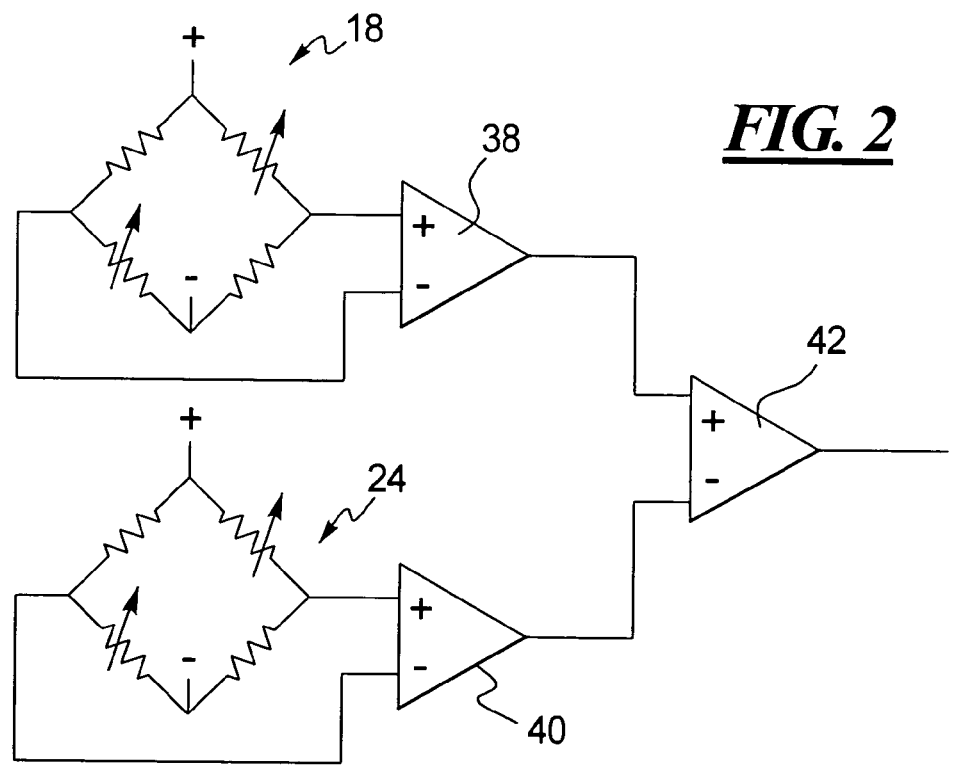
FIG. 2 illustrates a processor that can be used to process the outputs of two differential microstructure flow sensors.

Accordingly, FIG. 2 shows an arrangement to cancel changes in environmental conditions from the output of the first microstructure 18. As shown in FIG. 2, the temperature responsive microsensors (with arrows) of the first microstructure 18 are coupled in opposite legs of a Wheatstone bridge having two pairs of opposing terminals, one pair receiving a bridge input potential and the other pair forming a bridge output that is coupled to the input terminals of a first differential amplifier 38. Similarly, the temperature responsive microsensors (with arrows) of the second microstructure 24 are coupled in opposite legs of a Wheatstone bridge having two pairs of opposing terminals, one pair receiving a bridge input potential and the other pair forming a bridge output that is coupled to the input terminals of a second differential amplifier 40.

Thus, the output of the first differential amplifier 38 provides an output for the first microstructure 18, and the output of the second differential amplifier 40 provides an output for the second microstructure 24. A third differential amplifier 42 subtracts the output of the first differential amplifier 38 from the output of the second differential amplifier 40 so as to substantially cancel environmental effects, such as fluid pressure, temperature, orientation, etc, from the output of the first microstructure 18. (The supplies to the microheaters of the first and second microstructures 18 and 24 are not shown but are conventional.)

If an air/fuel ratio is to be sensed, any sensing error caused by ambient humidity can be eliminated through use of the absolute thermal conductivity sensor 10. Thus, the absolute thermal conductivity sensor 10 eliminates the need for an extra humidity sensor to sense ambient air. The extra humidity sensor is needed in prior art devices in order to increase the accuracy of sensing the air/fuel ratio at engine intakes when a reference sensor is exposed to ambient air.

Figure 3:
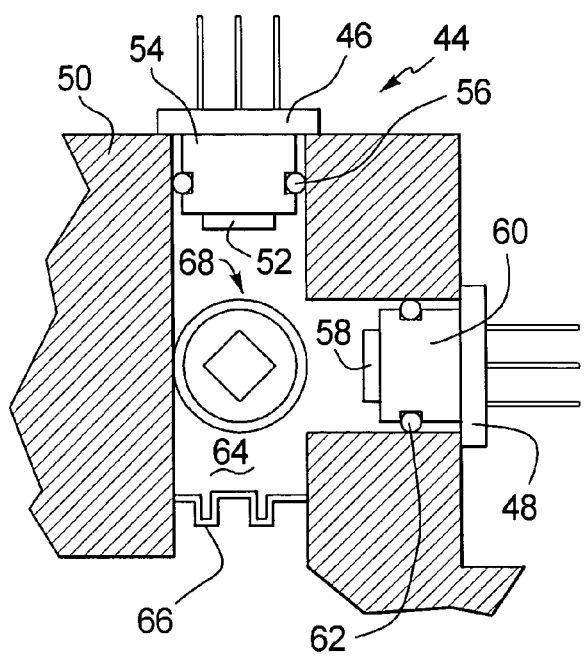
FIG. 3 illustrates an orientation sensor according to a second embodiment of the present invention.

FIG. 3 shows an orientation sensor 44 according to a second embodiment of the present invention. As shown in FIG. 3, the orientation sensor 44 includes a first microstructure sensor 46 and a second microstructure sensor 48 mounted to a housing 50.

The first microstructure sensor 46, for example, may comprise a first microstructure 52 supported by a first mounting block 54 secured to the housing 50. A first O-ring seal 56 fitted in a recess of the first mounting block 54 seals against leakage between the housing 50 and the first mounting block 54.

The second microstructure sensor 48, for example, may comprise a second microstructure 58 supported by a second mounting block 60 secured to the housing 50. A second O-ring seal 62 fitted in a recess of the second mounting block 60 seals against leakage between the housing 50 and the second mounting block 60.

Each of the first and second microstructures 52 and 58, for example, may be constructed in accordance with the microbridge disclosed in U.S. Pat. No. 4,683,159. Alternatively, each of the first and second microstructures 52 and 58 may be microbricks as discussed below. Thus, as shown in this patent, each of the first and second microstructures 52 and 58 may include a microheater element between a pair of temperature responsive microsensors.

Although not shown, shields such as shields 34 and 36 can be provided for the first and second microstructures 52 and 58 as discussed above. Alternatively, shields such as shields 34 and 36 can be provided with respect to FIGS. 1 and 5, and the devices shown in FIGS. 3, 4, 6, and 7 can be operated without such shields.

The housing 50 has a sealed chamber 64 containing a fluid that is common to both the first and second microstructures 52 and 58. A diaphragm 66 seals the sealed chamber 64 such that the first and second microstructures 52 and 58 are exposed to the common fluid in the sealed chamber 64. A fill fluid fills the sealed chamber 64. This fill fluid, for example, may be an inert gas or liquid, which ideally is close to the average composition of the fluid typically encountered as the sample fluid in contact with the first sensor.

Because the first and second microstructures 52 and 58 are mounted at 90° relative to one another and a common liquid (or pressurized gas) is sealed into the sealed chamber 64, the orientation sensor 44 with only the first and second microstructures 52 and 58 operates as a two-axis orientation sensor with intrinsic temperature and pressure compensation. That is, the gravity effects on the kinetics of the fluid within the sealed chamber 64 produce different responses from the first and second microstructures 52 and 58 and can be used as an indication of the orientation of the orientation sensor 44.

The circuit of FIG. 2 can be used to process the outputs of the first and second microstructures 52 and 58 so as to provide an output from the third differential amplifier 42 that indicates the two axis orientation of the differential thermal conductivity sensor 44 and that is compensated for temperature and pressure. Alternatively, a third microstructure could be provided for sensing the fluid in the chamber 64. In this case, a first circuit as in FIG. 2 could be provided for the first and third microstructures, a second circuit as in FIG. 2 could be provided for the second and third microstructures, and a third circuit as in FIG. 2 could be provided for the first and second microstructure. Thus, each pair of microstructures is used to cancel out the effects of environmental conditions such as fluid pressure, temperature, orientation, etc. from the orientation outputs. All together, each pair of sensors represents a tilt or acceleration sensor for one of the three spatial axes.

As further shown in FIG. 3, a third microstructure 68 with mounting block and O-ring may be provided so that the first, second, and third microstructures 52, 58, and 68 are orthogonal to one another and so that the third microstructure 68 is also exposed to the fluid in the fluid chamber 64. With this third microstructure 68, the orientation sensor 44 is a three axis orientation sensor.

Each pair of the first, second, and third microstructures 52, 58, and 68 can be processed by a corresponding circuit (such as shown in FIG. 2) to provide three separate outputs that collectively indicate three axis orientation. Alternatively, a fourth microstructure could be provided for sensing the fluid in the chamber 64. In this case, a first circuit as in FIG. 2 could be provided for the first and fourth microstructures, a second circuit as in FIG. 2 could be provided for the second and fourth microstructures, and a first circuit as in FIG. 2 could be provided for the third and fourth microstructures to provide a three axis orientation output. The fourth microstructure, thus, is used to cancel out the effects of environmental conditions such as fluid pressure, temperature, orientation, etc. from the orientation outputs.

Figure 4:
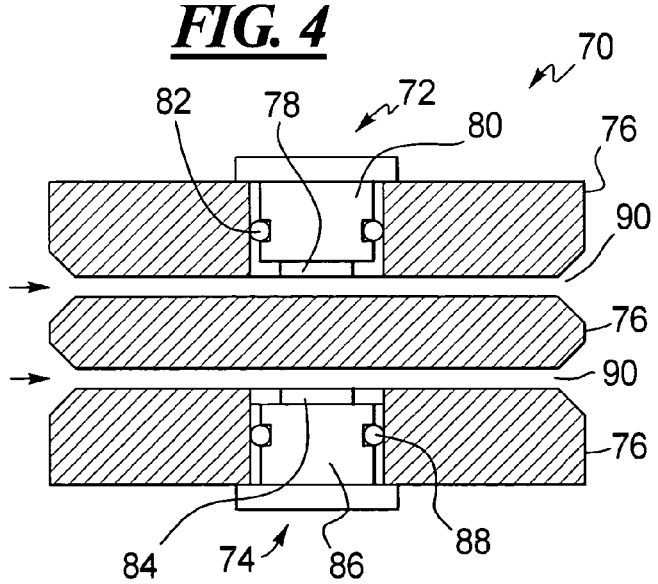
FIG. 4 illustrates a differential thermal conductivity sensor that can be used in gas chromatography according to a third embodiment of the present invention; and, FIGS. 5 and 6 illustrate rotation sensor according to a fourth embodiment of the present invention.

FIG. 4 shows a differential thermal conductivity sensor 70 according to a third embodiment of the present invention. For example, the differential thermal conductivity sensor 70 can be used in gas chromatography. As shown in FIG. 4, the differential thermal conductivity sensor 70 includes a first microstructure sensor 72 and a second microstructure sensor 74 mounted to a housing 76.

The first microstructure sensor 72, for example, may comprise a first microstructure 78 supported by a first mounting block 80 secured to the housing 76. A first O-ring seal 82 fitted in a recess of the first mounting block 80 seals against leakage between the housing 76 and the first mounting block 80.

The second microstructure sensor 74, for example, may comprise a second microstructure 84 supported by a second mounting block 86 secured to the housing 76. A second O-ring seal 88 fitted in a recess of the second mounting block 86 seals against leakage between the housing 76 and the second mounting block 86.

Each of the first and second microstructures 78 and 84, for example, may be constructed in accordance with the microbridge disclosed in U.S. Pat. No. 4,683,159. Thus, as shown in this patent, each of the first and second microstructures 78 and 84 may include a microheater between a pair of temperature responsive microsensors.

The housing 76 has a flow path 90 having a first portion containing a fluid that passes the first microstructure 78 in one direction and a second portion in which the fluid passes the second microstructure 84 in the opposite direction. In the example of FIG. 4, fluid in the flow path 90 flows from left to right through the first portion along the first microstructure 78 and from right to left through the second portion along the second microstructure 84. As shown by way of example in FIG. 4, the first and second portions of the flow path 90 are parallel to one another. In gas chromatography, the first portion the flow path 90 (to which the first microstructure 78 is exposed) carries the reference gas, and the second portion the flow path 90 (to which the second microstructure 84 is exposed) carries the separated reference and sample gases.

The differential thermal conductivity sensor 70, when used to implement a low cost gas chromatography differential thermal conductivity sensor, enables the sensing of small composition differences between the two equal flows forced past the first and second microstructures 78 and 84 that are closely spaced. A pressure drop such as across a restriction may be used to force the flow through the channel 90.

The distance between each of the first and second microstructures 78 and 84 and the channel 90 should be minimized for good measurement time resolution. Additionally, a minimum dead volume, such as $\leq 5$ nL, may be provided around the first and second microstructures 78 and 84 where the first and second microstructures interface with the channel 90. For example, the volume of space between the first microstructure 78 and the housing 76 may be filled with a filler or plug so that, as viewed in FIG. 4, the lower surface of the first microstructure 78 and the lower surface of the filler or plug form a smooth and/or coplanar surface with the housing 76 along the first portion of the channel 90. Similarly, the volume of space between the second microstructure 84 and the housing 76 may be filled with a filler or plug so that, as viewed in FIG. 4, the upper surface of the second microstructure 84 and the upper surface of the filler or plug form a smooth and/or coplanar surface with the housing 76 along the second portion of the channel 90. The use of microbrick sensors as described below can be used to minimize this dead volume.

The circuit of FIG. 2 can be used to process the outputs of the first and second microstructures 78 and 84 in the same manner as the outputs of the first and second microstructures 18 and 24 are processed such that the output from the first differential amplifier 38 can be used to identify the components of the fluid flowing through the channel 90.

Figure 5:
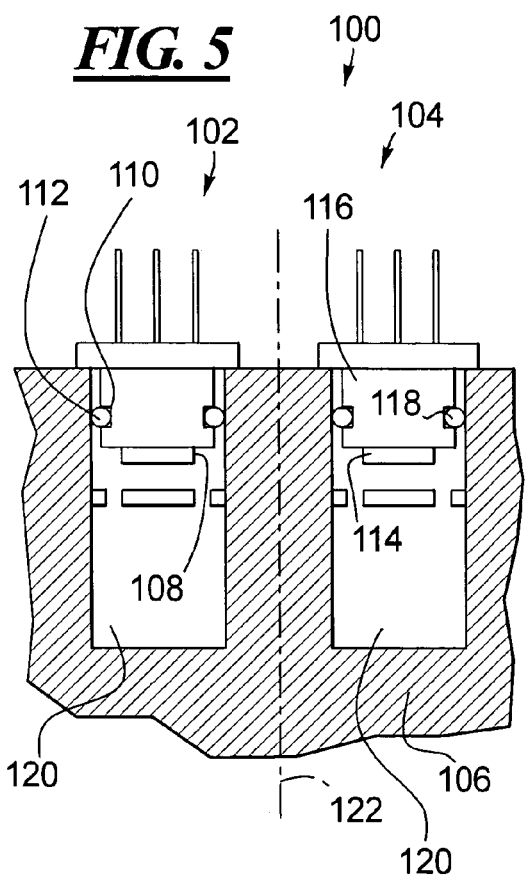
Figure 6:
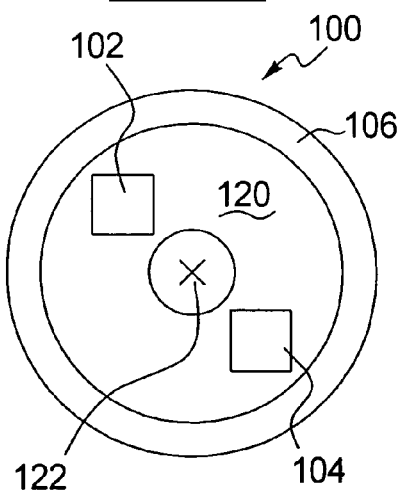

FIGS. 5 and 6 show a rotation sensor 100 according to a fourth embodiment of the present invention. As shown in FIG. 5, the rotation sensor 100 includes a first microstructure sensor 102 and a second microstructure sensor 104 mounted to a housing 106.

The first microstructure sensor 102, for example, may comprise a first microstructure 108 supported by a first mounting block 110 secured to the housing 106. A first O-ring seal 112 fitted in a recess of the first mounting block 110 seals against leakage between the housing 106 and the first mounting block 110.

The second microstructure sensor 104, for example, may comprise a second microstructure 114 supported by a second mounting block 116 secured to the housing 106. A second O-ring seal 118 fitted in a recess of the second mounting block 116 seals against leakage between the housing 106 and the second mounting block 116.

Each of the first and second microstructures 108 and 114, for example, may be constructed in accordance with the microbridge disclosed in U.S. Pat. No. 4,683,159. Thus, as shown in this patent, each of the first and second microstructures 108 and 114 may include a microheater between a pair of temperature responsive microsensors.

The housing 106 has a donut shaped chamber 120 containing a fluid. Accordingly, both of the first and second microstructures 108 and 114 are exposed to the fluid in the donut shaped chamber 120. The fluid contained in the donut shaped chamber 120 can be a gas such as nitrogen, argon, etc. Alternatively, the fluid contained in the donut shaped chamber 120 can be a liquid such as water, heptane, oil, etc.

As shown by the cross-sectional side view of FIG. 5 and the top view of FIG. 6, the housing 106 is able to rotate about an axis 122. Because of inertia, the fluid within the donut shaped chamber 120 tends to remain motionless with respect to the first and second microstructure sensors 102 and 104 when the housing 106 begins to rotate. Thus, the microstructure sensors 102 and 104 will experience a flow that represents rotation, rotation rate, rotational acceleration, and/or tilt, while canceling disturbances such as those caused by changes in orientation, pressure, and ambient temperature. For such applications, the fill fluid in the donut shaped chamber 120 is preferably liquid for greater inertial effects.

Proper selection of liquid viscosity (damping), cavity wall smoothness, and chamber height and width/radius ratio enables finding a tradeoff between sensitivity and after-run error, which have characteristic exponential rise and decay times to enable deconvolution of the desired rotation rate for the specified angular range of interest.

By subtracting the opposed flow signals from the microsensors of the first and second microstructures 108 and 124, the rotation effect is effectively summed, and linear acceleration and environmental effects are canceled. The circuit of FIG. 2 could be used for this purpose.

Figure 7:
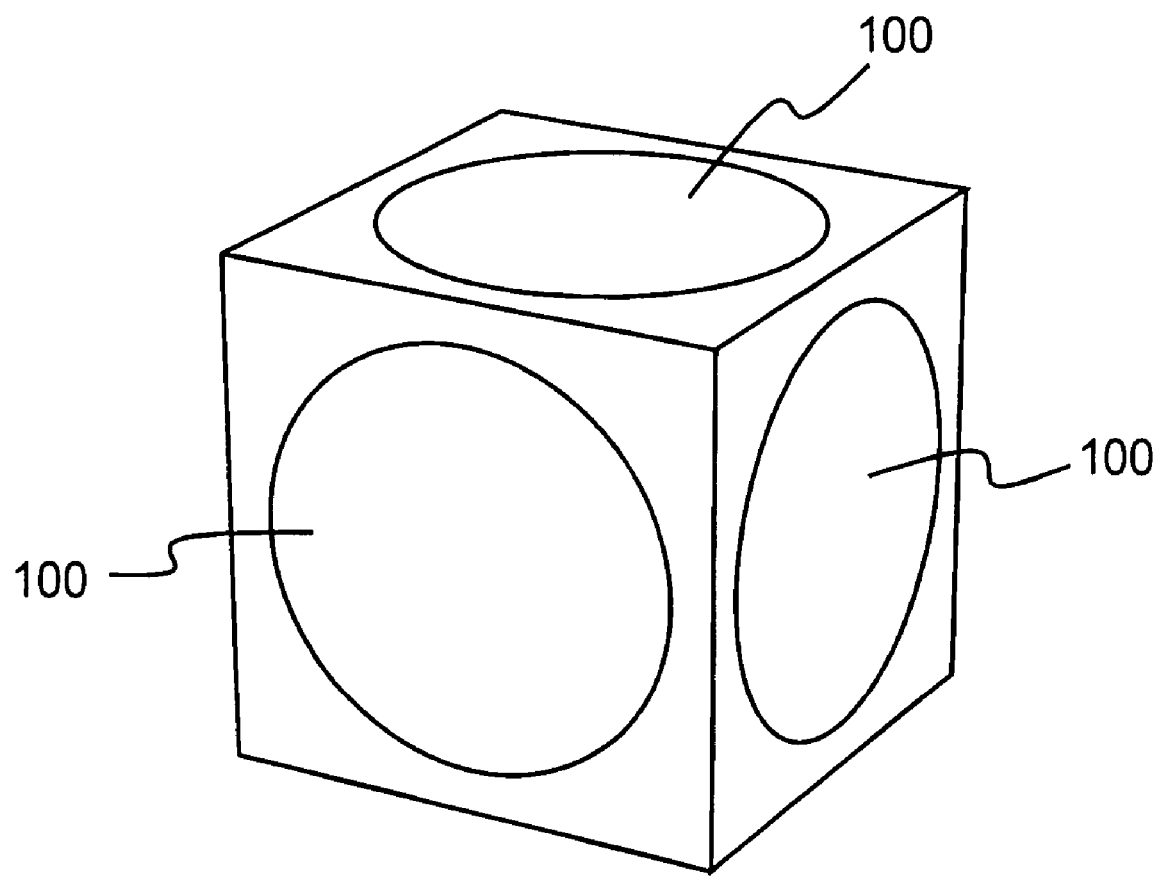
FIG. 7 illustrates a three axis rotation sensor that incorporates three of the rotation sensors shown in FIGS. 5 and 6.

Additionally, two rotation sensors 100 can be mounted orthogonally to one another so as to provide a two axis rotation sensor, or, as shown in FIG. 7, three rotation sensors 100 can be mounted orthogonally to one another so as to provide a three axis rotation sensor.

The absolute thermal conductivity sensor 10, the orientation sensor 44, the differential thermal conductivity sensor 70, and the rotation sensor 100 simultaneously eliminate first-order temperature, pressure, and orientation effects which disturb the operation of individual or single thermal conductivity (TO) sensors.

The absolute thermal conductivity sensor 10 senses concentration changes in stationary fluids, when no pressurized reference fluid is made available by the system, whereby such stationary reference is built into the sensor. Thus, the absolute thermal conductivity sensor 10 can be used to sense small changes in the composition of stationary fluids (gases or liquids) such as in air, process streams, and/or gas or liquid in fluid storage tanks (aircraft tanks, fuel cell processing tanks, etc.)

The differential thermal conductivity sensor 70 senses concentration changes in flowing fluids (gases or liquids), when a pressurized reference stream is made available by a system, such as a Gas Chromatography system. Also, the differential thermal conductivity sensor 70 can be used to sense small changes in a carrier gas stream, before and after a sample volume is added and separated into components. Moreover, the differential thermal conductivity sensor 70 has a sub-millisecond response time.

The rotation sensor 100 senses (with a fluid sealed in with the microstructures as shown in FIG. 5) either rotation or acceleration, separately, or sequentially, but not simultaneously, by taking advantage either of the inertia of the fluid fill in the chamber 120, or of the thermal microconvection driven by the microheaters of the first and second microstructures 108 and 114 to sense orientation or acceleration.

Off-the-shelf, relatively high volume microbridge or micro-membrane sensor chips can be used as the microstructures 18, 24, 52, 58, 78, 84, 108, and 114 of the sensors 10, 44, 70, and 100 to implement a low cost differential thermal conductivity sensor. Accordingly, the sensors 10, 44, 70, and 100 are more affordable than prior thermal conductivity sensors while providing good accuracy and insentivity to environmental conditions.

Certain modifications of the present invention have been discussed above. Other modifications will occur to those practicing in the art of the present invention. For example, as discussed above, off-the-shelf microbridge or micro-membrane sensor chips can be used as the microstructures 18, 24, 52, 58, 78, 84, 108, and 114 of the sensors 10, 44, 70, and 100.

Moreover, microbridges are suggested as examples of the microstructures 18, 24, 52, 58, 78, 84, 108, and 114. Microbridges are microdevices that include a heater, an upstream temperature responsive microsensor, and a downstream temperature responsive microsensor formed as a bridge over a well, typically in a silicon substrate. Instead, each of the microstructures 18, 24, 52, 58, 78, 84, 108, and 114 may be a corresponding Microbrick™ described in U.S. patent application Ser. Nos. 10/150,851 and 10/337,746. This type of device includes a microheater, an upstream temperature responsive microsensor, and a downstream temperature responsive microsensor formed on a substantially solid substrate such as a silicon substrate.

Furthermore, FIG. 2 illustrates a processor that can be used to form a difference between the outputs of two microstructure sensors. The processor of FIG. 2, however, may take alternative forms such as a computer, logic gates, programmable logic arrays, and/or other circuits or arrangements to form a difference between the outputs of two or more microstructure sensors.

Accordingly, the description of the present invention is to be construed as illustrative only and is for the purpose of teaching those skilled in the art the best mode of carrying out the invention. The details may be varied substantially without departing from the spirit of the invention, and the exclusive use of all modifications which are within the scope of the appended claims is reserved.

The invention claimed is:

1. A sensor comprising:
   a housing having a sealed chamber containing a fluid;
   a first microstructure sensor mounted to the housing so as to be exposed to the fluid in the sealed chamber, wherein the first microstructure sensor includes a microheater and at least one temperature responsive microsensor; and,
   a second microstructure sensor mounted to the housing so as to be exposed to the fluid in the sealed chamber, wherein the second microstructure sensor includes a microheater and at least one temperature responsive microsensor, and wherein the first and second microstructure sensors are mounted so as to sense a flow of the fluid in the sealed chamber.

2. The sensor of claim 1 wherein the housing has a rotation axis, wherein the sealed chamber comprises a sealed axi-symmetric chamber containing the fluid, and wherein the first and second microstructure sensors are mounted with respect to the axis so as sense a rotation of the housing about the axis based on the sensors' high sensitivity to the flow of the fluid relative to the housing.

3. The sensor of claim 1 wherein the housing has a rotation axis, and wherein the first and second microstructure sensors are mounted at an angle of substantially 90° with respect to one another so as to sense two-axis orientation of the housing, or 180° with respect to each other so as to sense one-axis orientation of the housing.

4. The sensor of claim 3 wherein the first microstructure sensor provides a first output, wherein the second microstructure sensor provides a second output, and wherein the orientation sensor further comprises an apparatus configured to combine the first and second outputs so as to optimize maximum signal and/or number of orientation axes on a measure of the orientation of the housing.

5. The sensor of claim 3 wherein the first and second microstructure sensors are assembled from available and low cost microstructures.

6. The sensor of claim 5 wherein the available and low cost microstructures comprise one from a group including microbridges, micromembranes and Microbricks (TM).

7. The sensor of claim 2 further comprising an apparatus arranged to subtract opposed flow signals from the first and second microstructures to effectively sum the rotation effect and cancel out linear acceleration and environmental effects.

8. The sensor of claim 2 wherein the fluid comprises a gas.

9. The sensor of claim 2 wherein the fluid comprises a liquid.

10. The sensor of claim 2 wherein the liquid comprises a high density, low viscosity, and chemically inert liquid, such as Fluorinert (TM).

11. The sensor of claim 2 wherein the first and second microstructure sensors are mounted in parallel to one another on opposite sides of the axis of the housing so as to sense rotation of the housing about the axis.

12. The sensor of claim 2 wherein the first microstructure sensor provides a first output, wherein the second microstructure sensor provides a second output, and wherein the rotation sensor further comprises an apparatus configured to combine the first and second outputs so as to reduce environmental influences on a measure of the rotation of the housing.

13. The sensor of claim 2 whereby more than two sensors are exposed to the rotational fluid flow, so that they can be switched to serve as 2 pairs of tilt and acceleration sensors and sense 2-axis tilt or acceleration.

14. The sensor of claim 2 wherein the first and second microstructure sensors are assembled from available and low cost microstructures.

15. The sensor of claim 14 wherein the available and low cost microstructures comprise microbridges.

16. The sensor of claim 14 wherein the available and low cost microstructures comprise Microbricks (TM).

17. The sensor of claim 14 wherein the available and low cost microstructures comprise micromembrane structures.

* * * * *